United States Patent [19]

Murfitt et al.

[11] 4,354,508
[45] Oct. 19, 1982

[54] ELECTRODE

[75] Inventors: Robert R. Murfitt, Chelmsford; Richard F. Burtt, Andover, both of Mass.

[73] Assignee: Vaughn Corporation, Salisbury, Mass.

[21] Appl. No.: 178,839

[22] Filed: Aug. 18, 1980

[51] Int. Cl.³ .............................................. A61N 1/04
[52] U.S. Cl. .................................... 128/798; 123/799; 123/802
[58] Field of Search ...................... 128/783, 791–793, 128/798, 799, 802, 803, 207.21, 639–641, 644

[56] References Cited

U.S. PATENT DOCUMENTS

| | | | |
|---|---|---|---|
| 2,047,308 | 7/1936 | Chapman | 128/798 |
| 3,721,246 | 3/1973 | Landis | 128/783 |
| 4,233,987 | 11/1980 | Feingold | 128/639 |
| 4,250,878 | 2/1981 | Jacobsen et al. | 128/803 X |
| 4,257,424 | 3/1981 | Cartmell | 128/641 |
| 4,328,814 | 5/1982 | Arkans | 128/640 |

Primary Examiner—Lee S. Cohen

Attorney, Agent, or Firm—Schiller & Pandiscio

[57] ABSTRACT

An improved electrode assembly for use in providing a stimulating current to a living body is disclosed. The assembly comprises a plurality of electrode modules electrically connected together in series with flexible electrical conductors, preferably in the form of a wire, so that, the modules and conductors form an integral assembly and so that in accordance with the method of the present invention the modules each can be selectively oriented and positioned on the skin with respect to one another enabling the assembly to follow the direction of an incision. In the preferred form the modules of the assembly are initially mechanically connected together with a single sheet having perforations so that the sheet can be torn along the perforations when separating the modules from one another. The number of modules applied to the skin can easily be reduced from the plurality by disconnecting the wire at the appropriate location so as to reduce the number of modules to the desired number.

11 Claims, 3 Drawing Figures

U.S. Patent  Oct. 19, 1982  4,354,508
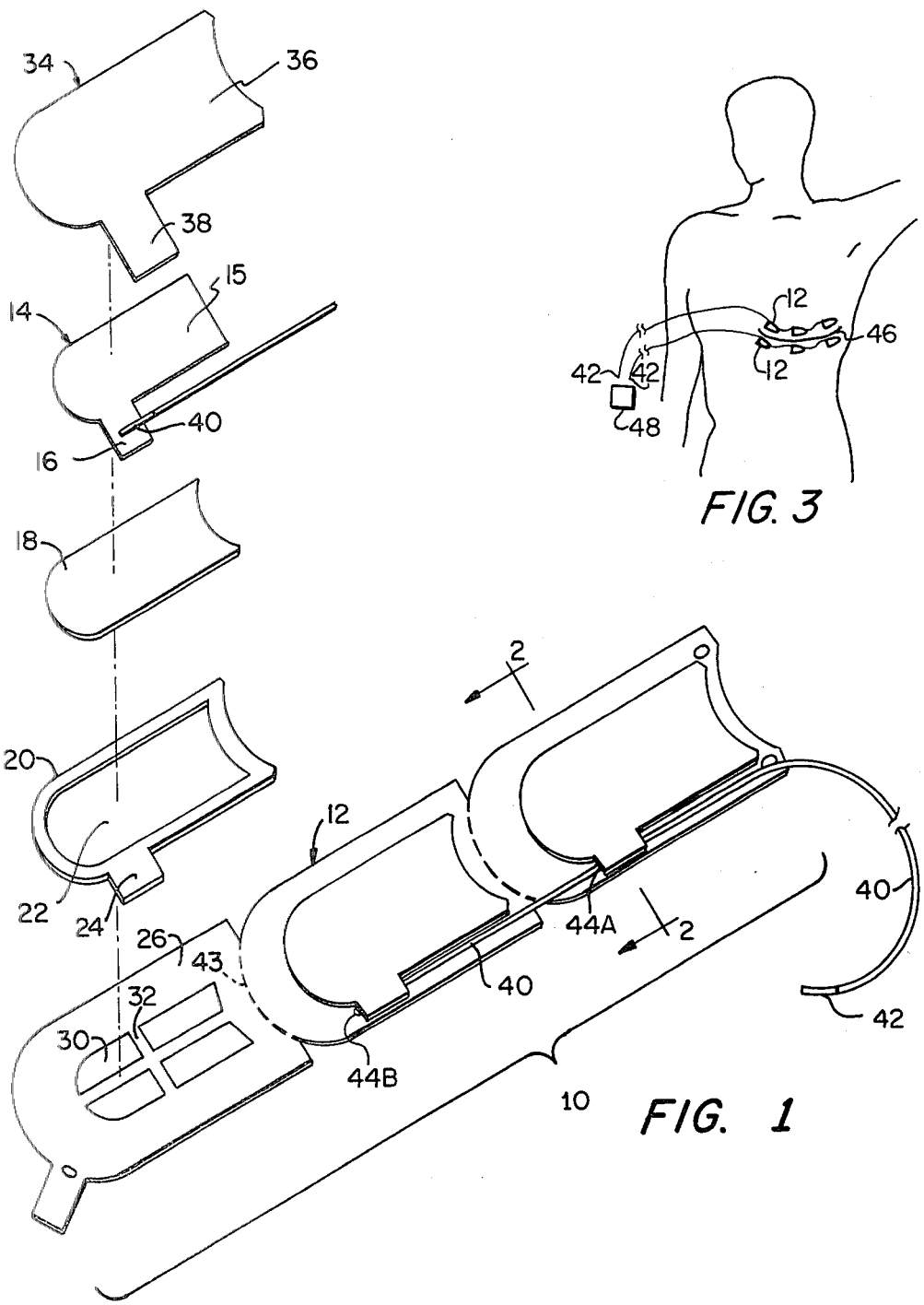
FIG. 1
FIG. 3
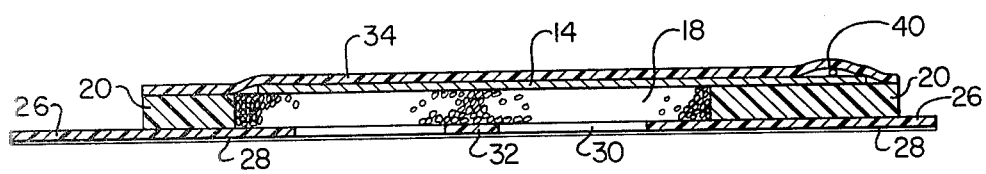
FIG. 2

ELECTRODE

The present invention relates to apparatus for providing a stimulating current to the skin of a living body, and more particularly to an improved electrode which is particularly useful in providing transcutaneous electrical nerve stimulation (TENS) and to an improved method of providing stimulating currents in a more selective manner.

The idea of using electric current to reduce or eliminate pain has been tried by serious researchers as well as promoted by quacks for many years. History even records the story of a Greek physician in the first century A.D. who used the shock of electric eels as a pain reliever.

Although the use of electric current to reduce or eliminate pain has been tried with some success in the United States in the last two decades, only in the last few years has the medical profession begun to take the idea seriously. One reason which may explain its growing acceptance among physicians is the fairly recent realization that many drugs are not only ineffective in pain control, but may have serious debilitating side effects.

Accordingly transcutaneous electrical nerve stimulation, as a noninvasive technique of relieving pain is gaining respectability as an effective means for reducing both acute pain, normally encountered in post-operative situations, and chronic pain. The TENS technique generally employs a pulse generator or stimulator which sends low-voltage current through two electrodes attached to the body. The current is typically provided in the form of a pulse train. Each pulse has an amplitude usually from 20 to 35 milliamps and is typically of about a 40 microsecond duration. The pulse repetition rate is often adjusted to the satisfaction of the patient, usually anywhere from 50 pulses per second to as many as 150 pulses per second. TENS stimulators are commercially available from such companies as Stimtech, Inc., Medtronic, Inc., and Medgeneral, all of Minneapolis, Minn.

When used to alleviate post-operative pain, an electrode is placed usually on each side of a surgical incision after the incision is closed, and the stimulator is attached to the electrodes to provide the necessary stimulating current.

It has been suggested that karaya is an excellent conductive material that can be placed between an electrode and the patient's skin. However, karaya provides a problem of maintaining the surgical area sterile. In order to overcome the problem of sterility several manufacturers are now manufacturing sterile TENS electrodes. Commercially available TENS electrodes (for an example of a prior art TENS electrode see U.S. Pat. No. 3,817,252 issued to Maurer on June 18, 1974) are usually relatively large rectangular shaped electrodes, e.g. 8 inches by 2 inches, which may be satisfactory for chronic pain applications when the pain is more generalized, but can be unsatisfactory in acute pain applications such as those often encountered in post-operative situations.

More specifically, where the surgical incision is long and straight, an 8"×2" electrode can be placed on each side of and very close to the incision so as to provide local stimulation when the appropriate current is applied. However, more often than not surgical incisions are not long and straight, but can be small and often, curved. For example, a common incision made in thoracic surgery is one which follows the bottom of the rib cage while incisions made in knee and hip surgery often curve around the area of the joint. As a consequence where the incision is relatively small the electrode may be too long; and in the case where the incision is curved, the electrode may have to be spaced from the area of pain by a greater than desirable amount so as to decrease the possibilities of providing effective stimulation and therefore relief to pain.

It is an object of the present invention to provide an improved electrode assembly which substantially overcomes or eliminates the problems associated with the prior art.

More specific objects of the present invention are to provide an improved electrode assembly for use in providing electrical stimulation which can be more easily adapted to the particular area to be stimulated, which can be shortened for smaller incisions and which can be applied to more closely follow the direction of curved incisions.

Another object of the present invention is to provide an improved method of providing electrical stimulation to a living body in a more selective manner.

These and other objects of the present invention are provided by an improved electrode assembly attachable to the skin of a living body for use with means for generating an electrical signal so as to provide electrical nerve stimulation. The improved integrally constructed electrode assembly comprises a plurality of electrode modules, each of an improved construction, and flexible electrically-conductive means for electrically connecting the modules in series with one another. In the preferred form the modules of the assembly are initially mechanically connected together with a single sheet having perforations so that the sheet can be torn along the perforations when separating the modules from one another. The individual modules can be selectively oriented and positioned with respect to one another when applied to the skin so as to follow any particular direction of application, while maintaining electrical contact with one another. The number of modules may be reduced from said plurality by disconnecting the said flexible electrically-conductive means at the appropriate place so as to reduce the number of modules to the desired number.

Other objects of the invention will in part be obvious and will in part appear hereinafter. The invention accordingly comprises the product possessing the features, properties and relation of components which are exemplified in the following detailed disclosure, and the scope of the application of which will be indicated in the claims.

For a fuller understanding of the nature and objects of the present invention, reference should be had to the following detailed description taken in connection with the accompanying drawing wherein:

FIG. 1 is a perspective view, partially exploded, of a preferred embodiment of an electrode assembly of the present invention;

FIG. 2 is a cross-sectional view taken along line 2—2 of FIG. 1; and

FIG. 3 shows a typical application of the electrode assembly in accordance with the method of the present invention.

Referring to FIGS. 1-2, the electrode modular assembly 10 is attachable to the skin of a living body for use with means for generating an electrical signal so as to provide transcutaneous electrical nerve stimulation of a predetermined area. The assembly includes a plurality of modules 12, three of which are shown in FIG. 1. Each module 12 comprises a first sheet 14 of an electrically-conductive material, such as stainless steel or the like. Sheet 14 preferably includes a generally rectangular main portion 15 having a curved edge at one end and an integral tab 16 extending from one side of the main portion 15.

A second sheet 18 is shaped and dimensioned to match and therefore contact the entire side of the main portion 15 of sheet 14. Sheet 18 may be any absorbent material, such as an opened cell foamed polyurethane or the like and is preferably preloaded with an appropriate electrically-conductive paste or gel.

A third sheet 20, preferably of a closed cell foam material such as expanded polyethylene, has a thickness approximately equal to sheet 18 and an aperture 22, sized to mate with and receive the sheet 18. Sheet 20 also includes tab 24 sized to completely support tab 16 of sheet 14 when main portion 15 is positioned on sheet 18 in the assembled position as shown in FIG. 2.

Sheet 26 includes a pressure-sensitive adhesive layer 28 on one side of the sheet for securing the module to the skin of the body which is to be stimulated. Sheet 26 and layer 28 may be any type of commercially available tape and preferably is of a hypoallergenic porous type such as the tape manufactured under the trademark Dermiclear by Johnson and Johnson. Sheet 26 includes at least one aperture 30 for exposing sheet 18 to the skin through sheet 26 provided with layer 28 when the module is assembled. Preferably, several apertures 30 are provided so as to define the cross-shaped supporting portion 32 of the sheet 26. Sheet 26 is made large in its width and length dimensions than sheet 20 so that sheets 18 and 20 are disposed in contact with the side of sheet 26 opposite layer 28, with tab 24 extending to the peripheral edge of sheet 26, while sheet 18 is exposed through apertures 30.

A cover sheet 34 made of an appropriate water repellant material, such as vinyl, includes a main portion 36 and tab 38. Cover sheet 34 is sized so that main portion completely covers sheet 14, sheet 18 and sheet 20, with tab 38 covering tab 16.

Flexible electrically-conductive means, in the form of wire 40 integrally connects each module 12 of the assembly 10 together in series by securing the wire to tab 16 of the sheet 14 of each module 12.

Assembled, the cover sheet 34 is secured at its edges to the edges of the sheet 26 by any suitable means such as a pressure-sensitive adhesive. The sheets 14, 18 and 20 are thus secured between sheets 26 and 34 with the sheet 14 being in full contact with sheet 18, and the sheet 18 disposed in aperture 22 of the sheet 20 between the sheet 14 and the adhesive sheet 26. A portion of the gel loaded sheet 18 is exposed through the apertures 30 of sheet 26. In this latter regard cross-shaped supporting portion 32 helps hold sheet 18 in place against electrically-conductive sheet 14 and makes it more difficult for the sheet 18 to be accidentally pulled through the apertures 30. Further, the exposed portion of wire 40 of each module is disposed between tab 38 of sheet 34 and tab 16 of sheet 14, while tab 16 is supported by tab 24 of sheet 20 so as to completely protect the uninsulated portion of the wire.

The wire 40 thus connects all the modules 12 of assembly 10 in series and terminates in plug 42 which is adapted to be plugged into a TENS stimulator of a type well known in the art.

In the preferred form of the assembly of the present invention a single sheet 26 can be utilized for all of the modules 12. As shown in FIG. 1, the sheet 26 can then be perforated at 43 so that the modules can be separated by tearing the sheet along the perforations.

In accordance with the method of the present invention a sufficient slack in the wire 40 between each module is provided. Each module 12 can be selectively oriented and positioned with respect to one another by separating sheet 26 at the perforations 43 so as to separate the modules while electrical contact is maintained between the modules through wire 40. The modules 12 can then be selectively oriented and positioned so that they easily conform to the direction of any surgical incision such as shown in FIG. 3 at 46. As shown one assembly of modules can be selectively secured along one side of the incision 46, while another assembly can be selectively secured along the other side of the incision. The plug 42 of each assembly is plugged into a stimulator 48 of the type well known in the art and the appropriate stimulating current is applied to the particular area selected by the placement of each of the modules. Where all of the modules are not necessary, the number of modules can easily be reduced by severing the select part of wire 40 such as shown at either point 44A or 44B so as to reduce the number of modules to the desired number. Thus, severing the wire at point 44A provides a single remaining module, while severing the wire at point 44B provides two remaining modules.

Since certain changes may be made in the above products without departing from the scope of the invention herein involved, it is intended that all matter contained in the above description or shown in the accompanying drawing shall be interpreted in an illustrative and not in a limiting sense.

What is claimed is:

1. An electrode assembly attachable to the skin of a living body for use with signal generating means for generating an electrical signal so as to provide electrical stimulation of a predetermined area of said body, said assembly comprising:

a plurality of electrode modules, each module comprising
(a) a first sheet of electrically-conductive material;
(b) a second sheet of porous material for retaining an electrically-conductive gel material;
(c) a third sheet of material having an aperture for receiving said second sheet of material;
(d) an adhesive sheet having an adhesive layer on one side of said adhesive sheet for securing each said module to the skin of said body, said adhesive sheet including an opening smaller in its cross-sectional dimension than said second sheet; and
(e) a cover sheet secured to the side of said adhesive sheet opposite said adhesive so as to secure said first, second and third sheets therebetween in order to maintain said first sheet in contact with said second sheet and said second sheet in the aperture of said third sheet between said first sheet and said adhesive sheet, and so as to expose a portion of said second sheet through the opening in said adhesive sheet;

flexible electrically-conductive means for electrically connecting the first sheets of said modules in series with one another;

means for electrically connecting said electrically-conductive means to said means for generating said electrical signal;

wherein the modules can each be selectively oriented and positioned with respect to the remaining modules when each module is applied to the skin of said body while maintaining electrical contact with one another, and the number of modules applied may be reduced from said plurality by severing said flexible electrically-conductive means at the appropriate location so as to reduce the number of modules to a desired number.

2. An electrode assembly according to claim 1, wherein said first sheet includes a tab portion, said conductive means being electrically connected to the tab of the first sheet of each said module.

3. An electrode assembly according to claim 2, wherein said cover sheet includes a tab portion covering said tab portion of said first sheet so as to protect said conductive means therebetween.

4. An electrode assembly according to claim 1, wherein said adhesive sheet includes an integral portion extending across said opening maintaining said second sheet in the aperture of said third sheet and in contact with said first sheet.

5. An electrode assembly according to claim 4, wherein said integral portion is a cross-shaped portion.

6. An electrode assembly according to claim 1, wherein said electrically-conductive means includes a wire, and said means for electrically connecting said electrically-conductive means includes a plug connected to said wire for electrically connecting said assembly to said signal generating means.

7. An electrode assembly according to claim 1 wherein said adhesive sheet of said modules is formed as a single sheet having perforations between each of said modules so that said modules can be separated from one another by tearing said adhesive sheet along said perforations.

8. A method of applying a stimulating current to a select area of the skin of a living body, said method comprising the steps of:

applying a plurality of electrode modules mechanically and electrically connected together to the area of the skin so that each of said modules is independently positioned and oriented in any desired direction with respect the others so as to form a predetermined pattern, and applying a current through said modules so as to provide said stimulating current to said area of the skin.

9. A method according to claim 8, wherein said select area of the skin includes an incision and said modules are positioned and oriented so as to follow said incision.

10. A method according to claim 9, wherein said modules are electrically connected together by a single wire and said step of applying said modules includes the step of severing said electrical wire connecting said modules so as to reduce the number of modules applied to the skin.

11. A method according to claim 9, wherein said step of applying a plurality of modules includes the step of applying two sets of said modules, one on each side of said incision.

* * * * *